US010219715B2

(12) United States Patent
Fisk

(10) Patent No.: US 10,219,715 B2
(45) Date of Patent: *Mar. 5, 2019

(54) BIOMEDICAL ELECTRODE HAVING LOW OXYGEN CONTENT

(71) Applicant: Pulse Technologies, Inc., Quakertown, PA (US)

(72) Inventor: Andrew E. Fisk, Philadelphia, PA (US)

(73) Assignee: Pulse Technologies, Inc., Quakertown, PA (US)

( * ) Notice: Subject to any disclaimer, the term of this patent is extended or adjusted under 35 U.S.C. 154(b) by 322 days.

This patent is subject to a terminal disclaimer.

(21) Appl. No.: 14/742,657

(22) Filed: Jun. 17, 2015

(65) Prior Publication Data

US 2016/0367159 A1 Dec. 22, 2016

(51) Int. Cl.
| | |
|---|---|
| *H01L 21/04* | (2006.01) |
| *A61B 5/04* | (2006.01) |
| *A61N 1/05* | (2006.01) |
| *B23K 26/00* | (2014.01) |
| *H01L 31/0224* | (2006.01) |
| *A61B 5/042* | (2006.01) |
| *B23K 26/0622* | (2014.01) |
| *B23K 26/362* | (2014.01) |

(52) U.S. Cl.
CPC ............... *A61B 5/042* (2013.01); *A61N 1/05* (2013.01); *B23K 26/0078* (2013.01); *B23K 26/0084* (2013.01); *B23K 26/0624* (2015.10); *B23K 26/362* (2013.01); *H01L 21/042* (2013.01)

(58) Field of Classification Search
CPC .......... A61N 1/04; A61N 1/05; H01L 21/042; H01L 31/0224
See application file for complete search history.

(56) References Cited

U.S. PATENT DOCUMENTS

| | | | |
|---|---|---|---|
| 5,318,572 A | 6/1994 | Helland et al. | |
| 5,571,158 A | 11/1996 | Bolz et al. | |

(Continued)

FOREIGN PATENT DOCUMENTS

WO  WO2007095549 A2  8/2007

OTHER PUBLICATIONS

Vorobyev, A.Y., and Chunlei Guo, "Femtosecond Laser Nanostructuring OfMetals." Optics Press, vol. 14, No. 6; Mar. 20, 2006; pp. 2164-2169.

(Continued)

*Primary Examiner* — Allen Porter, Jr.
(74) *Attorney, Agent, or Firm* — Massina Pat & TM Law

(57) ABSTRACT

A biocompatible, implantable electrode for electrically active medical devices. The implantable medical electrode has a surface geometry which optimizes the electrical performance of the electrode, while mitigating the undesirable effects associated with prior art porous surfaces. The electrode has an optimized surface topography for improved electrical performance. Such a electrode is suitable for devices which may be permanently implanted in the human body as stimulation electrodes, such as pacemakers, or as sensors of medical conditions. Such is achieved by the application of ultrafast high energy pulses to the surface of a solid, monolithic electrode material for the purpose of increasing the surface area and thereby decreasing its afterpotential polarization. In addition, the electrode material comprises a biocompatible metal having a minimal or eliminated amount of metal oxides which are detrimental to electrode performance.

20 Claims, 1 Drawing Sheet

(56) References Cited

U.S. PATENT DOCUMENTS

| | | |
|---|---|---|
| 6,799,076 B2 | 9/2004 | Gelb et al. |
| 2007/0225785 A1 | 9/2007 | Park et al. |
| 2007/0292667 A1 | 12/2007 | Laude et al. |
| 2008/0183260 A1 | 7/2008 | Nygren |
| 2008/0299289 A1 | 12/2008 | Fisk |
| 2011/0126410 A1 | 6/2011 | Capcelea et al. |
| 2011/0160821 A1 | 6/2011 | Jackson et al. |
| 2013/0085557 A1 | 4/2013 | Terasawa |
| 2013/0296678 A1 | 11/2013 | Larsen et al. |
| 2014/0357973 A1 | 4/2014 | Fisk |
| 2015/0017363 A1 | 6/2015 | Fisk |

OTHER PUBLICATIONS

Vorobyev, et al; Effect of Surface Structural Modifications on Absorptivity of Platinum in Multi-Pulse Femtosecond Laser Ablation; LFNM; Jun. 29, 2006; Kharklv, Ukraine; pp. 42-44.

BIOMEDICAL ELECTRODE HAVING LOW OXYGEN CONTENT

BACKGROUND OF THE INVENTION

Field of the Invention

The present invention relates to a biomedical, implantable electrode for electrically active medical devices. The electrode has an improved surface topography for enhanced electrical performance. Such an electrode is suitable for devices which may be permanently implanted in the human body as stimulation electrodes, for example, pacemakers or sensors of medical conditions. This is achieved by the application of ultrafast, high energy pulses to the surface of a solid, monolithic electrode material for the purpose of increasing the surface area and thereby decreasing its after-potential polarization. With some commonly used electrode substrate metals, there are oxidation and corrosion reactions which can take place in vivo and are detrimental to the performance of the electrode. The invention processes these materials via a high energy pulse to increase the performance while treating them in specific environments to limit the effects of the oxidation and corrosion which are detrimental to electrode performance.

Description of the Related Art

There is great commercial interest in producing active implantable devices which are typically electrodes used for the stimulation of tissue or the sensing of electrical biorhythms. The electrical performance of implantable electrodes can be enhanced by increasing the external surface area which is in contact with tissues inside the body. It is known that increasing the surface area of an implantable electrode increases the double layer capacitance of the electrode and reduces the after-potential polarization, thereby increasing device battery life, or allowing for lower capture thresholds, and improved sensing of certain electrical signals, such as R and P waves. It is known in the art to apply a coating to increase the surface area of the electrode thereby reducing the after-potential polarization. A reduction in after-potential polarization results in an increase in charge transfer efficiency by allowing increased charge transfer at lower voltages. This is of particular interest in neurological stimulation. Double layer capacitance is typically measured by means of electrochemical impedance spectroscopy. In this method an electrode is submerged in a electrolytic bath and a small cyclic wave is imposed on the electrode. The current and voltage response of the electrode/electrolyte system is measured to determine the double layer capacitance. The capacitance is the predominant factor in the impedance at low frequencies (<10 Hz) and thus the capacitance is typically measured at frequencies of 0.001 Hz-1 Hz.

Preset day biomedical, implantable electrodes are comprised of well known biocompatible metals. It is known to increase the surface are of such electrodes by laser exposing them under appropriate conditions. However, a problem with the exposure method is that the exposure atmosphere is air or contains significant amounts of oxygen, which leads to the formation of metal oxides on and near the electrode surface which produces poor performance. The electrodes of this invention have a much reduced, or virtually eliminated, amount of unwanted metal oxide content. One method of achieving this result is to conduct the laser exposure in an atmosphere having a much reduced or eliminated oxygen content. The choice of gaseous atmosphere can either displace oxygen in the reaction chamber or react with the electrode metal to form a substantially non-oxide surface.

The current state of the art for increasing the surface area of an implantable electrode is to apply a suitable coating to the surface of electrode substrates. A principal concern in any coating application is the joining of the substrate and coating material and the adhesion between them. In this regard, U.S. Pat. No. 5,571,158 shows a stimulation electrode having a porous surface coating whose active surface area is essentially larger than the surface area defined by the geometrical basic shape of the electrode. U.S. Pat. No. 6,799,076 discloses an electrode having a substrate with a first layer covering at least a portion of the substrate, and a second layer covering at least a portion of the first layer. The first layer consists of a carbide, nitride or carbonitride of titanium, vanadium, zirconium, niobium, molybdenum, hafnium, tantalum or tungsten. The second layer includes iridium. U.S. Pat. No. 5,318,572 teaches a high efficiency tissue stimulating and signal sensing electrode. A lead has a porous electrode of platinum-iridium with recessed areas or grooves formed into the surface. The grooves allow for acute electrode stabilization as a result of clot formation and endocardial tissue capture. At least one layer of a porous coating of 20-200 micron diameter spherical particles are deposited on the surface of the base electrode to obtain a porous macrostructure for promoting chronic tissue ingrowth. A microstructure surface coating is applied to increase the active surface area and enhance electrical efficiency by lowering electrochemical polarization and increasing electrical capacitance.

A particular concern for these techniques is that a section of coating might become dislodged in use and become an irritant. Current techniques for testing the adhesion of a coating to a substrate results in the destruction of the test piece which is costly and requires statistical evidence to validate the test method and sampling. A better alternative to a coating would be the modification of the electrode substrate material itself, thereby eliminating the issue of poor adhesion and the potential of coating particles becoming dislodged during use. Prior attempts to produce a suitable modified surface which does not include a coating have failed due to mechanical limitations. An example is found in U.S. patent publication 2011/0160821 where the surface is laser etched, thus producing ridges with features 25,000 nm to 250,000 nm. For a suitable electrode, the surface features need to be sub-millimeter, for example, from about 1 nm to about 1000 nm. Others have taught laser ablation of electrode surfaces, however, such techniques cannot achieve the nanometer scale feature size of this invention.

The present invention solves these issues by the application of ultra-fast energy pulses supplied to the surface. It has now been found that energy pulses delivered by means of an ultrafast laser produces surface structures on the order of 50 nm to 500 nm which is ideal for tissue stimulation. This process is produced not by laser etching and removal of material but by a restructuring of the surface. In the laser etching process of U.S. patent publication 2011/0160821 the surface is modified through the impingement of the laser, and the smallest feature that can be made equates to the size of the focused laser beam, which is limited by the wavelength of the laser, typically 200-1600 nm.

It has furthermore been found that an important factor in obtaining the desired surface topography for enhanced electrical performance is in the form of a three tiered surface structure. The three structural tiers are described in terms of nano, micro and macro structures. The nano-structures are described as nanoglobules which are manifested as rounded tubes or spherical globules which are almost powdery in appearance but well adhered to the surface. The sphericity of the nanoglobules decreases with an increasing number of laser irradiation pulses per spot. These nanoglobules are superimposed on a hillock-like microstructure in a periodic pattern determined by the wavelength of the laser where the lower the wavelength the smaller the period of the pattern. This microstructure pattern is superimposed on somewhat larger macro structure which resemble ranges of mesas. As discussed more fully below, the macro protrusions have a width in the range of from about 0.15 μm to about 50 μm; the micro protrusions have a width ranging from about 0.15 μm to about 5 μm; and the nano protrusions have a width ranging from about 0.01 μm to about 1 μm. In an embodiment of the invention, the surface may also have voids which extend down into the substrate surface in addition to these outwardly extending protrusions or uplifts.

SUMMARY OF THE INVENTION

The invention provides an electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 μm to about 50 μm; a plurality of discrete micro protrusions distributed on and extending outwardly from the macro protrusions, the micro protrusions having a width ranging from about 0.15 μm to about 5 μm; and a plurality of discrete nano protrusions distributed on and extending outwardly from the micro protrusions, the nano protrusions having a width ranging from about 0.01 μm to about 1 μm. which substrate comprises a biocompatible metal comprising at least one of titanium, nickel, zirconium, niobium, molybdenum, tantalum, hafnium, iridium, cobalt, platinum, steel, or alloys or combinations thereof, or an alloy of titanium, aluminum and vanadium, an alloy of platinum and iridium, an alloy of nickel and cobalt, titanium, an alloy of titanium, tantalum or combinations thereof which metal substrate has a maximum of 20% atomic percent of oxygen content in the form of an oxide of the metal.

The invention further provides a method for producing an electrode comprising providing a solid, monolithic substrate having an outer peripheral surface, which substrate comprises a biocompatible metal comprising at least one of titanium, nickel, zirconium, niobium, molybdenum, tantalum, hafnium, iridium, cobalt, platinum, steel, or alloys or combinations thereof, or an alloy of titanium, aluminum and vanadium, an alloy of platinum and iridium, an alloy of nickel and cobalt, titanium, an alloy of titanium, tantalum or combinations thereat and then exposing the outer peripheral surface to pulses of laser irradiation having a laser spot diameter ranging from about 1 μm to about 1000 μm, wherein the number of pulses of laser irradiation per spot, ranges from about 10 to about 1500 pulses, the pulse wavelength ranges from about 200 nm to about 1500 nm, the pulse width ranges from about 1 femtosecond to about 5 picoseconds; at a irradiance of from about 200 watts/cm$^2$ to about 5000 watts/cm$^2$; wherein the exposing of the outer peripheral surface is conducted in an gaseous atmosphere comprising at least 80% by weight of at least one of nitrogen, hydrogen, xenon, argon, helium, neon, krypton, xenon, radon, fluorine, chlorine, bromine, iodine, a hydrocarbon, or combinations thereof, to thereby provide the outer peripheral surface with a topography having a plurality of discrete macro protrusions distributed about and extending outwardly from the outer peripheral surface, the macro protrusions having a width in the range of from about 0.15 μm to about 50 μm; a plurality of discrete micro protrusions distributed on and extending outwardly from the macro protrusions, the micro protrusions having a width ranging from about 0.15 μm to about 5 μm; and a plurality of discrete nano protrusions distributed on and extending outwardly from the micro protrusions, the nano protrusions having a width ranging from about 0.01 μm to about 1 μm, which metal substrate has a maximum of 20 atomic percent of oxygen content in the form of an oxide of the metal.

DESCRIPTION OF THE INVENTION

Figure 1A:
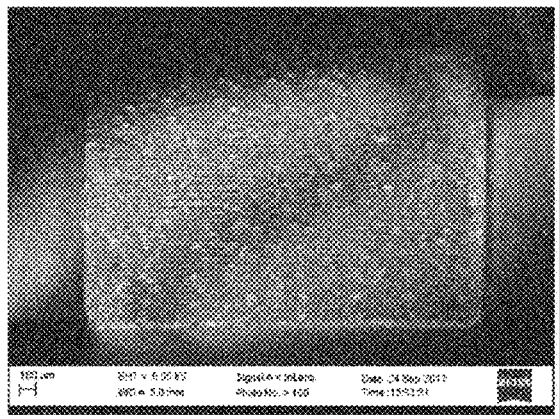
FIGS. 1A-1C show SEMs illustrating an exemplary substrate structure obtained according to an embodiment of the invention.

Surface morphologies of implanted biomedical electrodes are designed to improve interaction with surrounding tissues. The invention provides biological benefits such as a reduced likelihood of infection, and functional benefits such as improved electrical transfer. The invention produces features on biocompatible metals such as platinum by exposure to a femtosecond laser operating at various wavelengths. The invention realizes a performance advantage over typical prior art surface modifications by achieving an optimal surface geometry, which maximizes the effective surface area of the electrode while minimizing the after-potential polarization effect, thereby increasing charge transfer efficiency. After-potential polarization is the voltage remaining on an electrode after a stimulation pulse on the electrode from a device such as a pacemaker. It is a measure of how efficiently the charge is injected into the tissue.

It is known that the method for charge transfer in a medical electrode is by the charging and discharging of the electrical double layer capacitance formed on the surface of the electrode. This layer can be thought of as a simple parallel plate model in which the tissue to be stimulated is separated from the electrode surface by a barrier primarily of water, Na, K and Cl. The thickness of this layer is dictated by the concentration of the electrolyte in the body and is therefore uniform over the working life of the electrode. The thickness of an electrical double layer formed by an electrical conductor in 0.9% saline, i.e., body fluid is on the order of 1 nm and the expected thickness of the double layer capacitance formed in normal body electrolyte would be from about 0.5 nm to about 10 nm, more typically from about 5 to about 6 nm.

A typical human cell is on the order of from about 5,000 nm to about 10,000 nm in size. Because the cells are much larger than the layer and much smaller than the electrode surface, the cells can be thought of as being parallel to the surface of the electrode. As the non-polarized electrolyte (the electrolyte present but not participating in the electrical double layer) increases, the impedance of the tissue-electrode system increases. This is known as the solution resistance. The increased impedance results in a less effective charge transfer due to a dissipation of voltage along the solution resistance path. To minimize this impedance, the tissue to be stimulated should be as close to the electrode surface as possible. It would therefore be preferred, for these purposes, to have the electrode surface flat and placed parallel to the tissue.

The invention thus provides an electrode comprising a solid, monolithic substrate having an outer peripheral surface. The substrate comprises a biocompatible metal suitable for implanting within the tissues of a mammal. Examples non-exclusively include at least one of titanium, nickel, zirconium, chromium, niobium, molybdenum, tantalum, hafnium, iridium, cobalt, platinum, steel, or alloys or combinations thereof, or an alloy of titanium, aluminum and vanadium, an alloy of platinum and iridium, an alloy of nickel and cobalt, titanium, an alloy of titanium, tantalum; a nickel, cobalt, chromium, molybdenum alloy or combinations thereof. The substrate comprises at least 70 percent by weight of the metal, which is preferably platinum.

In one embodiment, the outer peripheral surface of an electrode has an area of from about 1 mm$^2$ to about 20 mm$^2$, preferably from about 3 mm$^2$ to about 12 mm$^2$. The electrode may have any suitable configuration or shape such as a tubular, flat, mushroom or corkscrew shape.

The outer peripheral surface has a topography defined by a plurality of discrete macro protrusions distributed about and extending outwardly from the outer peripheral surface (See FIG. 1A). In one embodiment, the macro protrusions are substantially uniformly distributed across the outer peripheral surface of the solid, monolithic substrate. In one embodiment, the macro protrusions have a width in the range of from about 0.15 .mu.m to about 50 .mu.m. In another embodiment, the macro protrusions have a width in the range of from about 0.2 .mu.m to about 30 .mu.m. In yet another embodiment, the macro protrusions have a width in the range of from about 1 .mu.m to about 20 .mu.m.

Figure 1B:
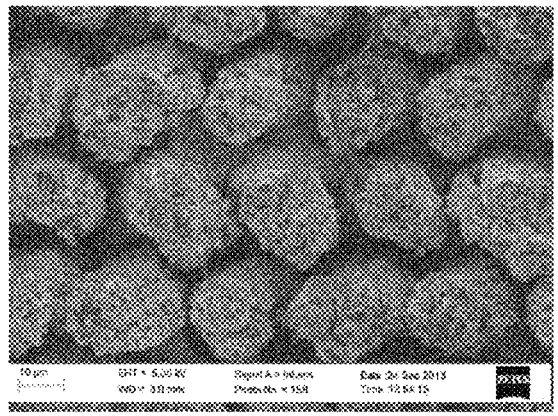

A plurality of discrete micro protrusions (hillock-like microstructure—See FIG. 1B) are distributed on and extend outwardly from the macro protrusions. In one embodiment, the micro protrusions have a width ranging from about 0.15 .mu.m to about 5 .mu.m. In another embodiment, the micro protrusions have a width in the range of from about 0.2 .mu.m to about 2 .mu.m. In yet another embodiment, the micro protrusions have a width in the range of from about 0.4 .mu.m to about 1.5 .mu.m. In one embodiment the micro protrusions are distributed across the macro protrusions in the form of periodic waves of the heights of the micro protrusions. It is believed that the periodic waves are caused and controlled by the wavelength of the laser irradiation.

Figure 1C:
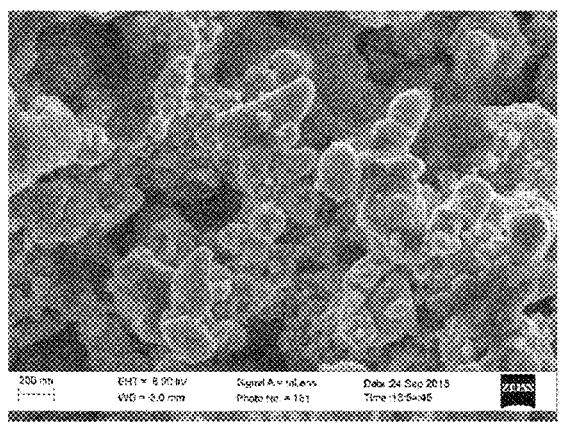

A plurality of discrete nano protrusions (nanoglobules—See FIG. 1C) are distributed on and extending outwardly from the micro protrusions. In one embodiment, the nano protrusions have a width ranging from about 0.01 .mu.m to about 1 .mu.m. In another embodiment, the nano protrusions have a width in the range of from about 0.02 .mu.m to about 1 .mu.m. In yet another embodiment the nano protrusions have a width in the range of from about 0.075 .mu.m to about 0.8 .mu.m. 4. In one embodiment, the nano protrusions are distributed across the micro protrusions in the form of tubes and/or globules. It is believed that the nano protrusions are caused and controlled by the number of pulses and the pulse duration. Without being held to a particular theory, it is believed that the macro, micro and nano protrusions are formed by the laser drilling voids in the substrate surface, and then the materials from the voids are re-deposited onto the substrate surface as these protrusions.

In another embodiment of the invention, in addition to these discrete macro, micro, and nano protrusions which extend outwardly from the substrate surface, the surface structure may have a laser induced array of voids whose length and depth depend on the laser parameters employed. Thus in this embodiment, the outer peripheral surface additionally has a topography with a plurality of voids distributed about the outer peripheral surface which extending a depth through the substrate. The voids have a depth through the substrate of from about 50 nm to about 500 nm, preferably from about 100 nm to about 250 nm. The voids have a width of from about 50 nm to about 500 nm, preferably of from about 100 nm to about 250 nm. The voids are spaced from adjacent voids a distance of from about 50 nm to about 250 nm.

An electrode according to the invention, is produced by exposing an outer peripheral surface of a solid, monolithic substrate of a biocompatible metal to pulses of laser irradiation. In one embodiment the laser has a spot diameter ranging from about 1 µm to about 1000 µm. In another embodiment, the laser has a spot diameter ranging from about 2 µm to about 250 µm, and in yet another embodiment, the laser has a spot diameter ranging from about 5 µm to about 200 µm. In one embodiment the number of pulses of laser irradiation per spot, ranges from about 10 to about 1500 pulses. In another embodiment, the number of pulses of laser irradiation per spot ranges from about 20 to about 1000, and in yet another embodiment, the number of pulses of laser irradiation per spot ranges from about 100 to about 500. In one embodiment the laser has a pulse wavelength which ranges from about 200 nm to about 1500 nm. In another embodiment, the pulse wavelength ranges from about 400 to about 1,000, and in yet another embodiment, the pulse wavelength ranges from about 400 to about 800. In one embodiment the laser pulse width ranges from about 1 femtosecond to about 5 picoseconds. In another embodiment the laser pulse width ranges from about 1 femtosecond to about 3 picoseconds. In one embodiment the laser irradiance ranges from about 200 watts/cm$^2$ to about 5000 watts/cm$^2$. The exposing may be conducted by traversing the spot of laser radiation across the outer peripheral surface of the solid, monolithic substrate at a rate of from about 50 mm/min to about 1000 mm/min, however, the rate is not critical to the invention and only affects the cost effective execution of the inventive method.

Examples of suitable lasers non-exclusively include a Coherent Libra-F Ti:Sapphire amplifier laser system, a Rofin Startfemto, and a Coherent AVIA laser. According to the invention, the resulting electrode has a polarization of about 1,000 mV or less, preferably about 500 mV or less, and more preferably about 200 mV or less. It has been determined that the lower the polarization of the electrode, the more optimized is the surface topography for improved electrical performance. The desirable characteristics of the surface, those being high double layer capacitance of the electrode and a low after-potential polarization effect, are enhanced when the surface area of the electrode is increased. A reduction in after-potential polarization results in an increase in charge transfer efficiency by allowing increased charge transfer at lower voltages. Thus a reduction of after-potential polarization increases device battery life, and improves sensing of certain electrical signals.

Laser exposure is conducted in an atmosphere having as little oxygen as possible in order to avoid metal oxide formation which detrimentally impacts electrode performance. Preferably, the laser exposure of the substrate is conducted while the substrate is enveloped in a gaseous atmosphere comprising at least one of nitrogen, hydrogen, xenon, argon, helium, neon, krypton, xenon, radon, fluorine, chlorine, bromine, iodine, a hydrocarbon, or combinations thereof. Nitrogen is preferred. The displacement of the oxygen could be accomplished by removal of the oxygen by creating a partial vacuum during processing with the aforementioned gases filling the partial vacuum. Preferably the atmosphere comprises at least 70% by weight of such gas, preferably at least about 90% by weight, more preferably at least about 95% by weight, still more preferably at least about 99% by weight. In another embodiment the atmosphere contains 100% of such gas or gases, which for this invention is defined as having no more than a trace amount of other generally unwanted gases such as oxygen.

The resulting electrode has no more than 20 atomic percent by of oxygen in the form of an oxide of the metal, preferably no more than about 10 atomic percent, more preferably no more than about 5 atomic percent and still more preferably no more than about 1 atomic percent. In another embodiment the electrode contains about 0% by weight of oxygen which for this invention is defined as having no more than a trace amount of oxygen. One method of measuring oxygen content is by XPS with ion milling. A measurement is taken and then the surface is milled using an ion beam to reveal a new surface. This continues for 300 nm from the top of a peak down and going into the material.

In use, the inventive electrode has at least one electrical connector electrically attached at an end thereof to the substrate. Typically, this may be a wire of a suitable material such as a biocompatible, conductive material such as platinum, silver, copper, a superalloy such as MP35N, or a superplastic such as Nitrol. MP35N alloy is a nonmagnetic, nickel-cobalt-chromium-molybdenum alloy possessing a unique combination of ultrahigh tensile strength (up to 300 ksi [2068 MPa]), good ductility and toughness, and excellent corrosion resistance. In addition, this alloy displays exceptional resistance to sulfidation, high temperature oxidation, and hydrogen embrittlement. In one embodiment, the other end of the wire is connected to an electrical pulse generator such as a cardiac pacemaker. In another embodiment, the other end of the wire is connected to an electrical measurement device such as a sensor of biological conditions, or a voltage recording device.

The following non-limiting examples serve to illustrate the invention.

Example 1

In this example a proximal ring electrode made of Pt10Ir with a surface area of approximately 16 sq mm was treated using 100 µJ of energy contained in a 35 micron diameter focused laser beam of 1030 nm wavelength light. The laser on-time was approximately 200 fs with a repetition frequency of 50 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was ambient air. The resulting polarization was 45 mV.

Example 2—Comparative

In this example a proximal ring electrode made of titanium with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was air. The resulting polarization was 115 mV.

Example 3—Comparative

In this example a proximal ring electrode made of titanium with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was argon. The resulting polarization was 140 mV.

Example 4

In the another example a proximal ring electrode made of titanium with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was nitrogen. The resulting polarization was 45 mV.

Example 5—Comparative

In the another example a proximal ring electrode made of titanium with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was oxygen. The resulting polarization was 199 mV.

Example 6—Comparative

In the another example a proximal ring electrode made of MP35N® with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was air. The resulting polarization was 100 mV.

Example 7

In the another example a proximal ring electrode made of MP35N® with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated The actual energy profile is larger than the recorded focal diameter which gives an overlap or laser irradiation between the adjacent spots. The environment for this example was argon. The resulting polarization was 55 mV.

Example 8

In the another example a proximal ring electrode made of MP35N® with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was nitrogen. The resulting polarization was 60 mV.

Example 9—Comparative

In the another example a proximal ring electrode made of MP35N® with a surface area of approximately 16 sq mm was treated using 20 µJ of energy contained in a 35 micron diameter focused laser beam of 1030=wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was oxygen. The resulting polarization was 115 mV.

Example 10—Comparative

In the another example a proximal ring electrode made of 316L stainless steel with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was air. The resulting polarization was 105 mV.

Example 11

In the another example a proximal ring electrode made of 316L stainless steel with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was argon. The resulting polarization was 60 mV.

Example 12

In the another example a proximal ring electrode made of 316L stainless steel with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated. The actual energy profile is larger than the recorded focal diameter which gives an overlap or laser irradiation between the adjacent spots. The environment for this example was nitrogen. The resulting polarization was 65 mV.

Example 13—Comparative

In the another example a proximal ring electrode made of 316L stainless steel with a surface area of approximately 16 sq mm was treated using 20 µJ of energy contained in a 35 micron diameter focused laser beam of 1030 nm wavelength light. The laser on-time was approximately 200 fs with a repetition frequency of 100 kHz. The laser treated the surface with 100 pulses before moving on to the next spot. Each spot was separated by 35 microns in both the x and y directions and the electrode was manipulated until the entire surface had been treated The actual energy profile is larger than the recorded focal diameter which gives an overlap or laser irradiation between the adjacent spots. The environment for this example was oxygen. The resulting polarization was 135 mV.

Table 1 shows the results:

TABLE 1

| Polarization (mV) | Air | Ar | N | O |
| --- | --- | --- | --- | --- |
| Pt10Ir | 45 (Example 1) | — | — | — |
| Ti | 115 (Example 2) | 140 (Example 3) | 45 (Example 4) | 199 (Example 5) |

TABLE 1-continued

| Polarization (mV) | Air | Ar | N | O |
|---|---|---|---|---|
| MP35N® | 100 (Example 6) | 55 (Example 7) | 60 (Example 8) | 115 (Example 9) |
| 316L | 105 (Example 10) | 60 (Example 11) | 65 (Example 12) | 135 (Example 13) |

For electrodes made of platinum and its alloys there is very little oxidation or corrosion in vivo although their major fault is the cost of such materials. With other commonly used more cost effective materials such as titanium, titanium alloys, cobalt/nickel alloys and steel there are oxidation and corrosion reactions which can take place in vivo and be detrimental to the performance of the electrode. The preceding examples show that with the displacement of an oxidizing atmosphere the more cost effective materials can be used. Example 1 is included as a reference to a high performing electrode made of Pt alloy. This example is a benchmark to the others. In all examples where nitrogen was used as the displacement gas the resulting polarization values are similar to that of the benchmark example. For examples 3, 7 and 11 the displacement gas was argon. While this choice of displacement gas was suitable for examples 7 and 11 it was not suitable for example 3. Titanium is one of the most widely known getter materials and as such it is difficult to control the oxidation of its surface, MP35N® and 316L however are known to be oxidation resistant at room temperature. It is therefore concluded that for the case of example 3 the argon was ineffective in displacing the bulk of oxygen from the working area during processing. It is further hypothesized that the atomic weight of the argon caused the unsuitable conditions by not allowing a good mixture of gases. For example 4 where nitrogen is used to displace the oxygen the titanium electrode also has the advantage of forming stable TiN compounds which prevent the growth of native oxides at room temperature. It is concluded that cost effective alternatives to electrodes made of platinum or platinum alloys can be realized so long as the oxidation and corrosions of the electrode is inhibited. The examples show that by using a displacing atmosphere electrodes made of titanium, 316L and MP35N achieve performance similar to that is platinum alloys.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An electrode comprising a solid, monolithic substrate having an outer peripheral surface; the outer peripheral surface having a topography defined by a plurality of discrete macro protrusions distributed about and extending outwardly from the outer peripheral surface, the macro protrusions having a width in the range of from about 0.15 µm to about 50 µm; a plurality of discrete micro protrusions distributed on and extending outwardly from the macro protrusions, the micro protrusions having a width ranging from about 0.15 µm to about 5 µm; and a plurality of discrete nano protrusions distributed on and extending outwardly from the micro protrusions, the nano protrusions having a width ranging from about 0.01 µm to about 1 µm; which substrate comprises a biocompatible metal comprising at least one of titanium, nickel, zirconium, chromium, niobium, molybdenum, tantalum, hafnium, iridium, cobalt, platinum, steel, or alloys or combinations thereof, or an alloy of titanium, aluminum and vanadium, an alloy of platinum and iridium, an alloy of nickel and cobalt, titanium, an alloy of titanium, tantalum; a nickel, cobalt, chromium, molybdenum alloy or combinations thereof which metal substrate has a maximum of 20 atomic percent of oxygen content in the form of an oxide of the metal.

2. The electrode of claim 1 wherein the metal substrate has a maximum of 10 atomic percent oxygen content in the form of an oxide of the metal.

3. The electrode of claim 1 wherein the metal substrate comprises platinum.

4. The electrode of claim 1 wherein the macro protrusions are substantially uniformly distributed across the outer peripheral surface of the solid, monolithic substrate.

5. The electrode of claim 1 wherein the micro protrusions are distributed across the macro protrusions in the form of periodic waves of the heights of the micro protrusions.

6. The electrode of claim 1 wherein the nano protrusions are distributed across the micro protrusions in the form of tubes and/or globules.

7. The electrode of claim 1 wherein the macro protrusions have a width in the range of from about 0.2 µm to about 30 µm; the micro protrusions have a width in the range of from about 0.2 µm to about 2 µm; and the nano protrusions have a width in the range of from about 0.02 µm to about 1 µm.

8. The electrode of claim 1 wherein the macro protrusions have a width in the range of from about 1 µm to about 20 µm; the micro protrusions have a width in the range of from about 0.4 µm to about 1.5 µm; and the nano protrusions have a width in the range of from about 0.075 µm to about 0.8 µm.

9. The electrode of claim 1 wherein the outer peripheral surface further comprises a plurality of voids distributed about the outer peripheral surface and extending a depth through the substrate; said voids having a depth through the substrate of from about 50 nm to about 500 nm; and said voids having a width of from about 50 nm to about 500 nm; said voids being spaced from adjacent voids a distance of from about 50 nm to about 250 nm.

10. The electrode of claim 1 which has a configuration suitable for implanting within the tissues of a mammal.

11. The electrode of claim 1 having an outer peripheral surface area of from about 1 mm$^2$ to about 20 mm$^2$.

12. The electrode of claim 1 further comprising at least one electrical connector electrically attached at an end thereof to the substrate.

13. The electrode of claim 12 further comprising an electrical pulse generator attached to another end of said electrical connector.

14. The electrode of claim 12 further comprising an electrical measurement device attached to another end of said electrical connector.

15. A method which comprises implanting the electrode of claim 1 within the tissues of a mammal.

16. A method for producing an electrode comprising providing a solid, monolithic substrate having an outer peripheral surface, which substrate comprises a biocompatible metal comprising at least one of titanium, nickel, zirconium, chromium, niobium, molybdenum, tantalum, hafnium, iridium, cobalt, platinum, steel, or alloys or combinations thereof, or an alloy of titanium, aluminum and vanadium, an alloy of platinum and iridium, an alloy of nickel and cobalt, titanium, an alloy of titanium, tantalum; a nickel, cobalt, chromium, molybdenum alloy or combinations thereof, and then exposing the outer peripheral surface to pulses of laser irradiation having a laser spot diameter ranging from about 1 μm to about 1000 μm, wherein the number of pulses of laser irradiation per spot, ranges from about 10 to about 1500 pulses, the pulse wavelength ranges from about 200 nm to about 1500 nm, the pulse width ranges from about 1 femtosecond to about 5 picoseconds; at a irradiance of from about 200 watts/cm$^2$ to about 5000 watts/cm$^2$; wherein the exposing of the outer peripheral surface is conducted in an gaseous atmosphere comprising at least 80% by weight of at least one of nitrogen, hydrogen, xenon, argon, helium, neon, krypton, xenon, radon, fluorine, chlorine, bromine, iodine, a hydrocarbon, or combinations thereof, to thereby provide the outer peripheral surface with a topography having a plurality of discrete macro protrusions distributed about and extending outwardly from the outer peripheral surface, the macro protrusions having a width in the range of from about 0.15 μm to about 50 μm; a plurality of discrete micro protrusions distributed on and extending outwardly from the macro protrusions, the micro protrusions having a width ranging from about 0.15 μm to about 5 μm; and a plurality of discrete nano protrusions distributed on and extending outwardly from the micro protrusions, the nano protrusions having a width ranging from about 0.01 μm to about 1 which metal substrate has a maximum of 20 atomic percent of oxygen content in the form of an oxide of the metal.

17. The method of claim 16 wherein the exposing is conducted by traversing the spot of laser radiation across the outer peripheral surface of the solid, monolithic substrate at a rate of from about 50 mm/min to about 1000 mm/min.

18. The method of claim 16 wherein the laser has a spot diameter ranging from about 2 μm to about 250 μm; the number of pulses of laser irradiation per spot ranges from about 20 to about 1000; the laser has a pulse wavelength which ranges from about 400 to about 1,000; and the laser pulse width ranges from about 1 femtosecond to about 3 picoseconds.

19. The method of claim 16 wherein the resulting metal substrate has a maximum of 10 atomic percent of oxygen content in the form of an oxide of the metal.

20. The method of claim 16 wherein the metal substrate comprises at least 70 percent by weight of platinum, and the gaseous atmosphere comprises at least 70 percent by weight of nitrogen.

* * * * *